United States Patent [19]

Okabe et al.

[11] Patent Number: 4,766,603
[45] Date of Patent: Aug. 23, 1988

[54] APERTURE DEVICE OF RADIATION DIAGNOSTIC APPARATUS

[75] Inventors: Kanichi Okabe, Tochigi; Hirotsugu Suzuki, Ootawara; Kohsaku Nishio, Ootawara; Katsuhiko Koyama, Ootawara, all of Japan

[73] Assignee: Kabushiki Kaisha Toshiba, Kawasaki, Japan

[21] Appl. No.: 928,389

[22] Filed: Nov. 10, 1986

Related U.S. Application Data

[63] Continuation of Ser. No. 672,194, Nov. 16, 1984.

[30] Foreign Application Priority Data

Nov. 18, 1983 [JP] Japan ................... 58-216008
Dec. 13, 1983 [JP] Japan ................... 58-234571

[51] Int. Cl.⁴ ............................................. G21K 1/04
[52] U.S. Cl. .................................. 378/152; 378/41; 378/150; 378/158; 378/162
[58] Field of Search ............... 378/41, 147, 150-152, 378/158, 204-205, 42, 99; 358/111

[56] References Cited

U.S. PATENT DOCUMENTS

| Re. 21,964 | 12/1941 | Leishman | 378/42 |
|---|---|---|---|
| 3,228,291 | 1/1966 | Miller | 378/150 |
| 3,287,561 | 11/1966 | Ingles | 378/152 |
| 3,643,095 | 2/1972 | Shuster | 378/151 |
| 3,947,689 | 3/1976 | Wagner | 378/151 |
| 424,137,460 | 1/1979 | Fitzsimmons et al. | 378/151 |
| 4,246,488 | 1/1981 | Hura | |
| 4,266,139 | 5/1981 | Sportelli et al. | 378/147 |
| 4,392,239 | 7/1983 | Wilkens | 378/152 |
| 4,393,402 | 7/1983 | Keyes et al. | 378/99 |
| 4,400,825 | 8/1983 | Boggi et al. | 378/150 |
| 4,445,226 | 4/1984 | Brody | 378/99 |
| 4,464,778 | 8/1984 | Goldmann | 378/150 |
| 4,472,828 | 9/1984 | Ferlic | 378/147 |
| 4,482,918 | 11/1984 | Keyes et al. | 358/111 |
| 4,489,426 | 12/1984 | Grass et al. | 378/147 |
| 4,544,949 | 10/1985 | Kurihara | 378/42 |

FOREIGN PATENT DOCUMENTS

| 0074596 | 3/1983 | European Pat. Off. | |
| 0083756 | 7/1983 | European Pat. Off. | |
| 0125622 | 11/1984 | European Pat. Off. | 378/157 |
| 2728999 | 1/1979 | Fed. Rep. of Germany | |
| 2440014 | 5/1980 | France | |
| 0195545 | 5/1982 | Japan | |
| 0000699 | 6/1982 | Japan | |

OTHER PUBLICATIONS

"X-Ray Aperture Device", by Nishio et al., translation of Kokai No. 58-195545.
"Movable Aperture Device in Twin Focus X-Ray Tube Apparatus", by Seisaku-sho, translation of Kokai No. 59-699.

Primary Examiner—Craig E. Church
Assistant Examiner—John C. Freeman
Attorney, Agent, or Firm—Finnegan, Henderson, Farabow, Garrett & Dunner

[57] ABSTRACT

An aperture device defines X-ray beams emitted from X-ray focal points L and R spaced apart from each other along the first direction. This defining operation is performed along the first direction and a second direction crossing the first position, thereby shaping a rectangular X-ray radiation area. Blades defining the two edges of the X-ray beam along the first direction and blades defining two edges of the X-ray beam along the second direction are supported by engaging portions into which screw portions of screw rods are screwed and engaging portions slidably fitted around round portions of the screw rods, respectively. When the screw rods are rotated by activation of corresponding stepping motors, the corresponding engaging portions are moved parallel to the screw rods. The respective blades can be variably moved along the first or second direction, thereby forming an X-ray radiation area having any shape in any position.

9 Claims, 9 Drawing Sheets

APERTURE DEVICE OF RADIATION DIAGNOSTIC APPARATUS

This is a continuation of application Ser. No. 672,194 filed Nov. 16, 1984.

BACKGROUND OF THE INVENTION

The present invention relates to an aperture device of a radiation diagnostic apparatus capable of performing stereoscopic and monoscopic radiography or fluoroscopy and, more particularly, to an aperture device for precisely aligning a radiation area with a predetermined area.

An X-ray diagnosis apparatus having radiographic and fluoroscopic functions has been used in X-ray diagnosis of circulatory organs so as to perform angiography of cerebral, heart and abdominal areas. A conventional X-ray diagnostic apparatus is illustrated in FIG. 1. A U-shaped arm 12 is supported on a vertical support 10 to be rotatable around a horizontal axis. Horizontal, reciprocal arms 14 and 20 are mounted at two ends of the arm 12. An X-ray tube 16 and an X-ray aperture device 18 are mounted on the arm 14. An X-ray fluoroscopic image intensifier (to be referred to as an I.I hereafter) 22, a cine camera 24 and a television camera 26 are mounted on the arm 20. The arm 20 also has an X-ray film changer 28 for X-ray radiography. When a patient 32 lying on a table top 30 is positioned between the X-ray tube 16 and the film changer 28, the X-ray emitted from the X-ray tube 16 passes through the patient 32. A transmitted X-ray image is detected by the film changer 28. This radiographic or fluoroscopic position can be adjusted by reciprocal movement of the arms 14 and 20 and rotation of the arm 12.

In cardiac and coronary angiography, X-rays emitted from two focal points are used to obtain an X-ray image, thereby obtaining a stereoscopic image. Three-dimensionally branched blood vessels in a complicated structure can be rendered more distinct. In order to observe the stereoscopic transmitted image, a stereo cine camera and a stereo projector have been recently developed. As a result, static or dynamic stereoscopic observation or stereo observation by several observers in an observation room can be performed.

In stereo radiography or fluoroscopy, the X-ray radiation area is defined by the X-ray aperture device 18, as shown in FIG. 2. High-speed electron beams are supplied to two positions L and R of a rotary anode 34 of the X-ray tube 16, and conical X-ray beams 36 and 38 are emitted from these two positions. These X-ray beams 36 and 38 are defined by fixed blades 40 and 44 and moving blades 42, 46 and 48 and then irradiate the patient 32.

In this conventional X-ray diagnostic apparatus, in order to change the X-ray radiation area in the stereoscopic view, a beam component of the X-ray beam 36 at the side of the X-ray beam 38 and a beam component of the X-ray beam 38 at the side of the X-ray beam 36 are not subjected to stopping since the blades 40 and 44 are fixed in position, as shown in FIG. 3. An unnecessary X-ray component irradiating the patient 32 is represented by a hatched area in FIG. 3. When a distance SID (source to image distance) between the X-ray focal points R and L and an imaging surface 50 changes, the radiation area of the X-ray beam 36 does not match with that of the X-ray beam 38. As a result, a clear X-ray image cannot be obtained. Therefore, the radiography must be performed at the predetermined distance SID.

FIG. 4 is an enlarged view illustrating the aperture device 18 used in adjusting an area of the radiation received by the patient. Before radiation, the positions of the moving blades 42, 46 and 48 are adjusted by utilizing light rays from lamps 52 ard 54. The lamps 52 and 54 are located at positions to coincide with the X-ray focal points R and L through mirrors 56 and 58, respectively. The light rays from the lamps 52 and 54 irradiate the same area as that of X-rays from the X-ray focal points R and L. Thus, positions of the blades are adjusted such that the light rays from the lamps 52 and 54 irradiate a predetermined area prior to X-ray radiation. The adjustment of the X-ray radiation area can be performed in an over-tube system X-ray diagnostic apparatus wherein the X-ray tube 16 is located above the patient 32. However, in an under-tube system apparatus wherein the arm 12 is rotated by a half revolution thus moving the X-ray tube below the patient 32, the light rays from the lamps are shielded by the table top 30, thereby preventing pre-adjustment of the X-ray radiation area. In the under-tube system, the relatively compact X-ray tube 16 is located below the table top 30, so that the height of the table top 30 can be decreased and operability can be improved. In addition, in the under-tube system, an amount of X-ray exposure of the patient 32 can be decreased (especially, his crystalline lenses) as compared with the amount of exposure by the over-tube system. Even though the under-tube system has these advantages, it is inconvenient that the X-ray radiation area cannot be adjusted prior to X-ray radiation. Although the under-tube system prevents pre-adjustment of the radiation area, this problem can be overcome by using an I.I. When a large diameter I.I having the same size as the photographing film is incorporated in the X-ray diagnosis apparatus, it becomes large, thus making it impractical. In addition, when the lamps 52 and 54 and the mirrors 56 and 58 are also mounted in the apparatus, the apparatus becomes larger.

SUMMARY OF THE INVENTION

It is an object of the present invention to provide an aperture device of a radiation diagnostic apparatus which can define X-rays to form a radiation area so as to be precisely identical with a predetermined diagnosis area in stereoscopic radiography and fluoroscopy.

According to the present invention, there is provided an aperture device of a radiation diagnostic apparatus which can define first and second radiation beams emitted from two radiation focal points which are spaced apart from each other along a first direction. The aperture device comprises: first and second blades, made of a radiation shielding material and movable along the first direction, for respectively defining two edges of a first radiation beam along the first direction; first and second driving means for respectively driving said first and second blades; third and fourth blades, made of a radiation shielding material and movable along the first direction, for respectively defining two edges of a second radiation beam along the first direction; third and fourth driving means for respectively driving said third and fourth blades; fifth and sixth blades, made of a radiation shielding material and movable along a second direction cross to the first direction, for respectively defining two edges of each of the first and second radiation beams along the second direction; and fifth and sixth drive means for respectively driving said fifth and sixth blades; whereby the first radiation beam is defined by said first, second, fifth and sixth blades in a rectangular shape, and the second radiation beam is defined by said third, fourth, fifth and sixth blades in a rectangular shape.

According to the aperture device of the radiation diagnostic apparatus of the present invention, the first, second, third, fourth, fifth and sixth blades can be positioned by the first, second, third, fourth, fifth and sixth driving means with high precision, respectively. Therefore, the radiation area can be formed to be identical with the predetermined diagnosis area with high precision. The radiation beams emitted from the two focal points can match on the patient with high precision, thereby eliminating unnecessary radiation.

DETAILED DESCRIPTION OF THE PREFERRED EMBODIMENT

Figure 1:
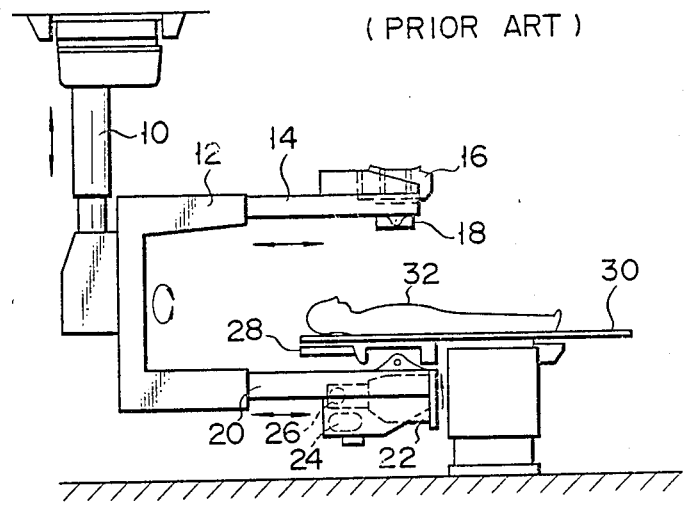
FIG. 1 is a schematic view showing a conventional X-ray diagnostic apparatus.
Figure 2:
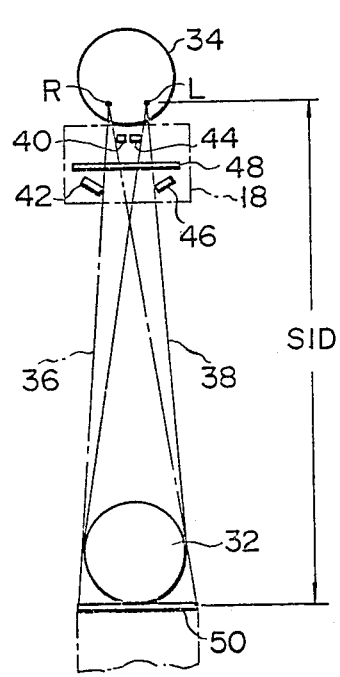
FIGS. 2 and 3 are representations showing a conventional X-ray aperture device.
Figure 3:
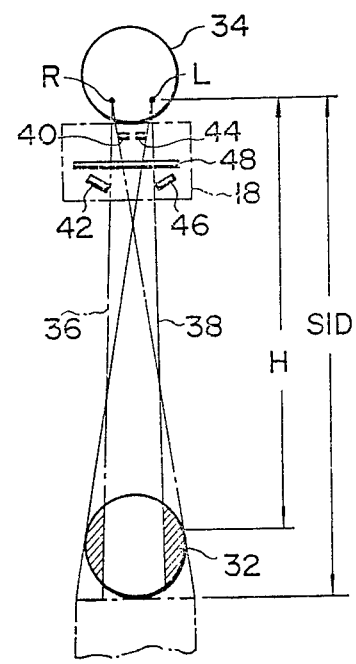
Figure 4:
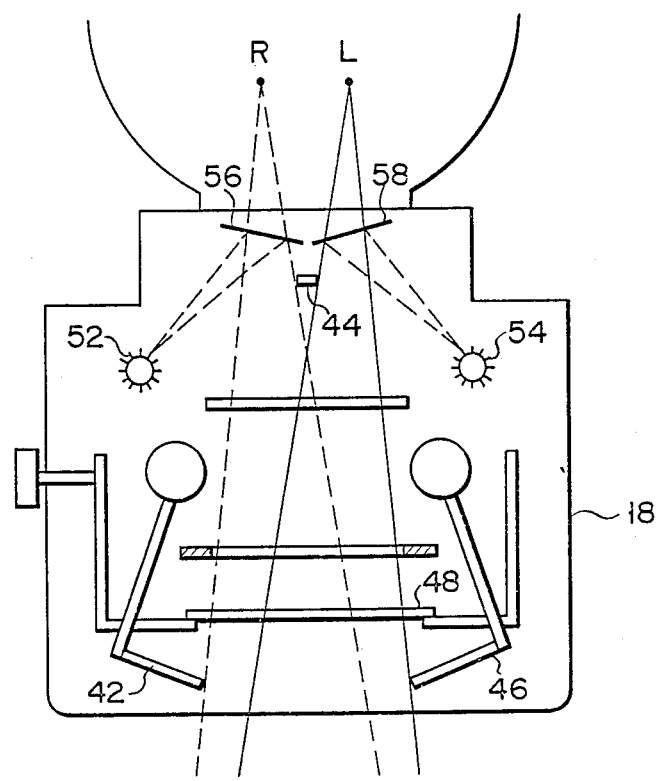
FIG. 4 is an enlarged view of the aperture device shown in FIGS. 2 and 3.
Figure 5:
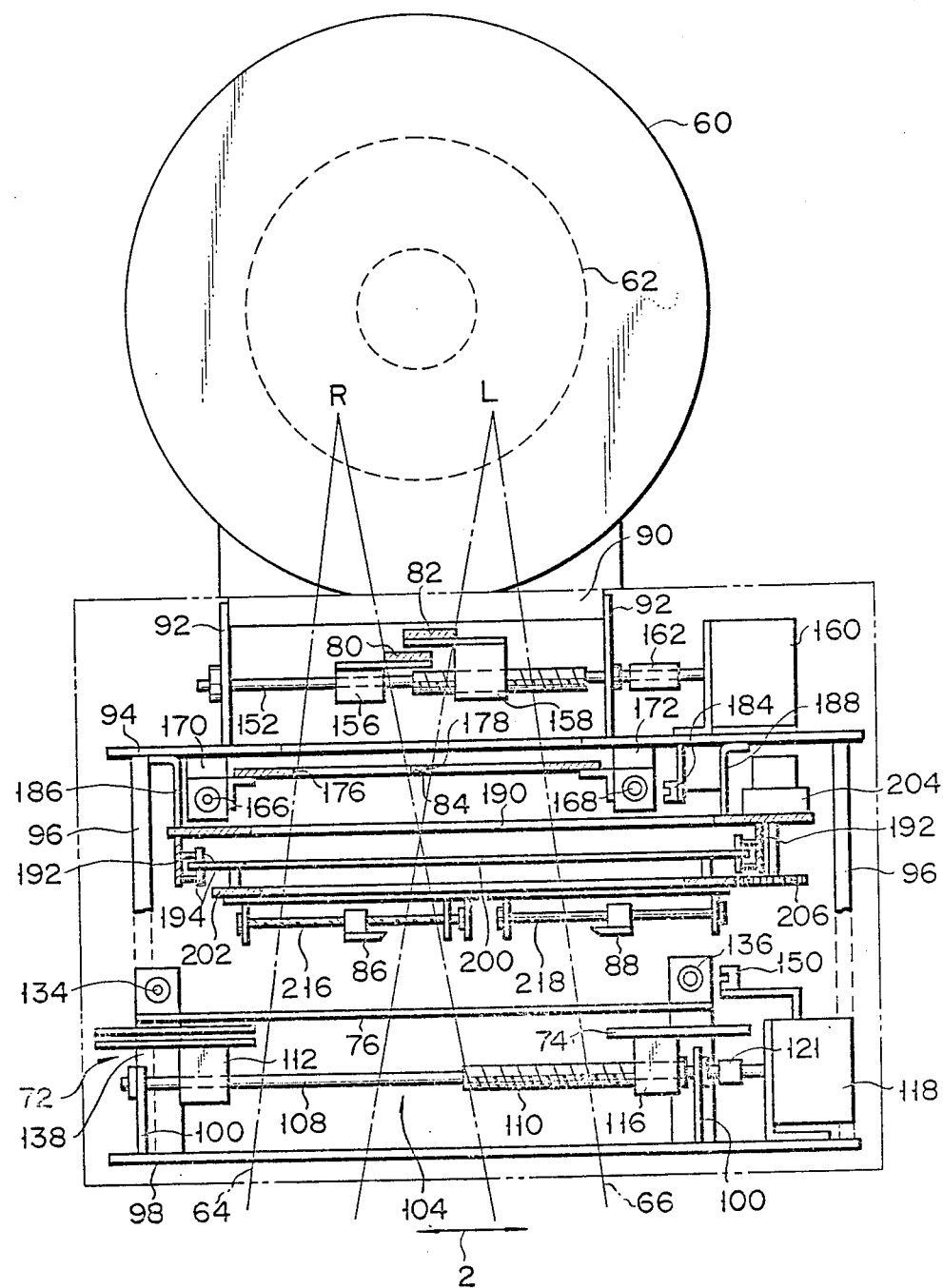
FIG. 5 is a sectional front view of an aperture device according to an embodiment of the present invention.
Figure 6:
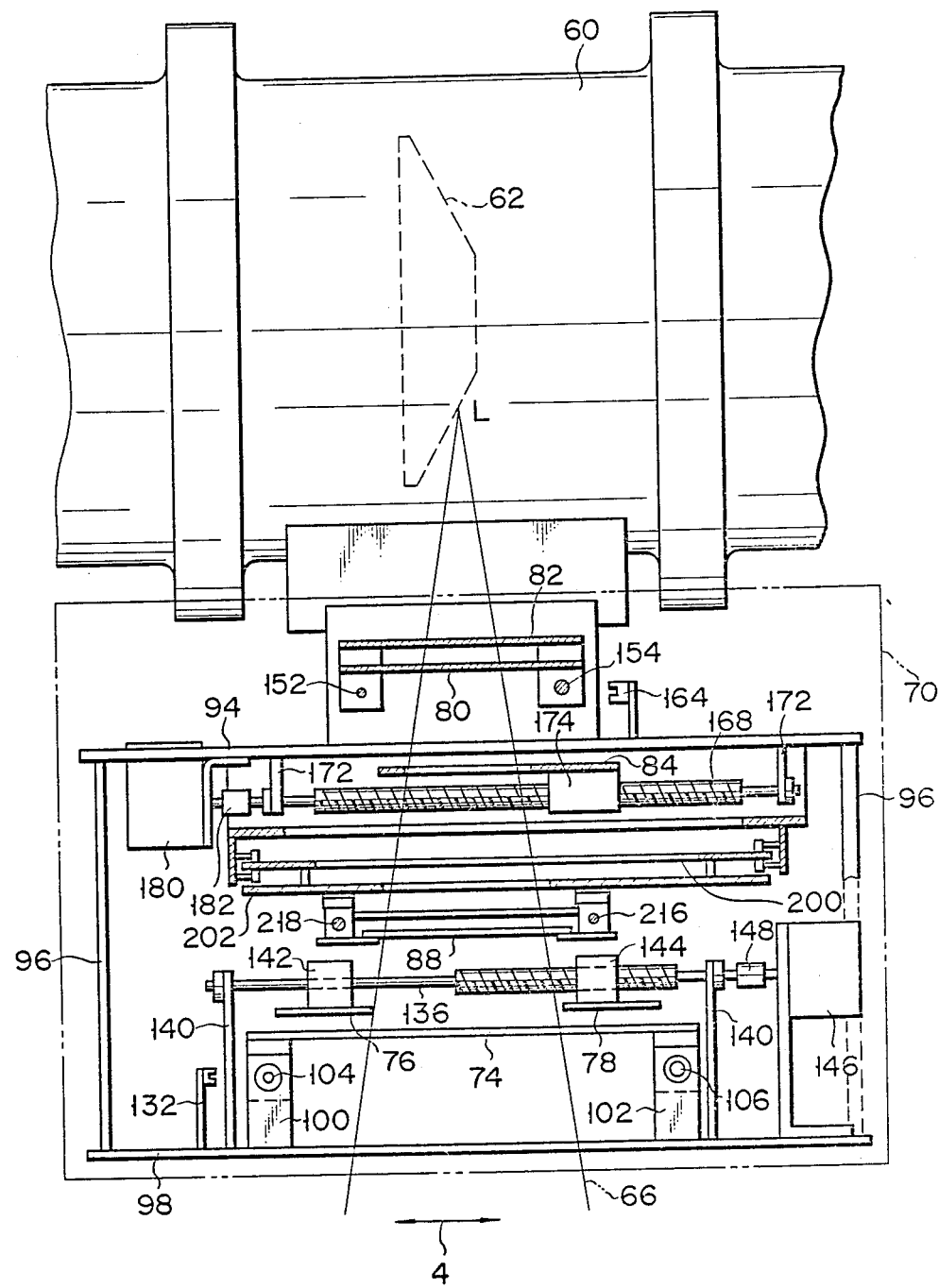
FIG. 6 is a side sectional view of the aperture device shown in FIG. 5.

FIG. 5 is a sectional front view of an aperture device of an X-ray diagnostic apparatus according to an embodiment of the present invention, and FIG. 6 is a side sectional view thereof. Two conical X-ray beams 64 and 66 are emitted from two focal points R and L in a rotary anode 62 of an X-ray tube 60. Referring to FIGS. 5 and 6, assume that the X-ray tube 60 is located immediately above the patient and that the axes of the X-ray beams 64 and 66 look toward the center of the imaging surface. An aperture device 70 is arranged at the lower end of the X-ray tube 60. The aperture device 70 incorporates six blades 72, 74, 76, 78, 80 and 82 for shaping a rectangular radiation area at the time of X-ray radiography. A blade 84 and compensation filters 86 and 88 are arranged between the blades 80, 82 and the blades 76, 78. The blade 84 forms a circular X-ray radiation area when X-ray fluoroscopy is performed by an image intensifier. A horizontal base 90 is fixed on the X-ray tube 60. A pair of supports 92 are fixed on the base 90 and are parallel to each other. A horizontal base 94 is fixed at the lower end of the supports 92. Supports 96 are vertically suspended from the base 94. A base 98 is horizontally fixed at the lower ends of the supports 96.

Figure 7:
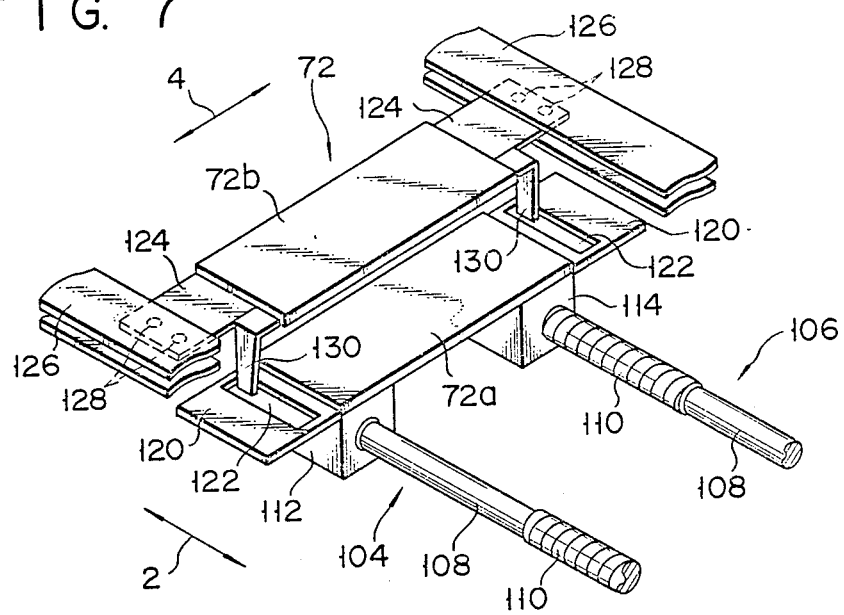
FIG. 7 is an enlarged perspective view of blades of a double structure.

The X-ray focal points R and L are defined as the right and left focal points. Referring to FIG. 5, a pair of supports 100 opposing along the right-and-left direction indicated by arrow 2 is erected on the base 98. As shown in FIG. 6, two supports 102 are also erected on the base 98 so as to be opposed to each other along the arrow 2. Screw rods 104 and 106 are rotatably supported by the respective support pairs 100 and 102 through corresponding bearings. The screw rods 104 and 106 are parallel to each other along the direction of arrow 2. Each of the screw rods 104 and 106 has a round rod portion 108 in FIG. 5 and in FIG. 7 (a perspective view showing the vicinity of the blades 72) and a screw portion 110 having a threaded portion thereon. The screw portions 110 of the screw rods 104 and 106 constitute the right and left portions of the rods 104 and 106, respectively. The blades 72 comprise two blades 72a and 72b, as shown in FIGS. 5 and 7. The blade 72a crosses over a pair of engaging portions 112 and 114. The round portion 108 of the screw rod 104 is inserted in the engaging portion 112, so that the engaging portion 112 can reciprocate along the round portion 108. However, the screw portion 110 of the screw rod 106 is screwed into the engaging portion 114, so that the engaging portion 114 can reciprocate along the screw rod 106 upon rotation thereof. The blade 74 crosses over a pair of engaging portions 116 in the same manner as the blades 72. The screw portion 110 of the screw rod 104 is screwed into the engaging portion 116. The blade 74 can reciprocate along the screw rod 104 upon rotation of the screw rod 104. The screw rods 104 and 106 are coupled to stepping motors 118 (shown only one side) through couplings 121, respectively. The blades 72a and 74 are moved in the direction of arrow 2 upon rotation of the motors 118 coupled to the screw rods 106 and 104.

As can be seen in FIG. 7, blades 72 have a double structure consisting of the blades 72a and 72b. Two ends of the blade 72a have ears 120 extending along the direction of arrow 4. A rectangular hole 122 extending along the direction of arrow 2 is formed in each of the ears 120. The two ends of the blade 72b have ears 124 extending along the direction of arrow 4. Each of the ears 124 is inserted between double-structured support plates 126 extending along the direction of arrow 2 and can be slidably supported along the longitudinal direction of the support plates 126. Projections 128 are formed on each ear 124 clamped between the support plates 126. The projections 128 provide a frictional force when the ear 124 is moved between the support plates 126. L-shaped lock portions 130, located along the direction of arrow 2, are formed at two ends of the blade 72b. The distal ends of the L-shaped lock portions 130 are inserted in the holes 122, respectively. Thus, when the blade 72a is moved along the direction of arrow 2, the blade 72b is also moved in the same direction. When the blade 72a is moved along an opposite direction, each of the lock portions 130 is moved by a distance corresponding to the length of the hole 122 and is further moved together with the blade 72a along the direction of arrow 2.

Referring again to FIG. 6, position sensor 132 is arranged on the base 98 for each of the blades 72 and 74. The position sensor 132 generates a reference signal when the distal ends of the blades 72 and 74 are at a central position immediately below the central position between the two focal points L and R. When this sensor generates a detection signal, the blades 72a and 74 are located at the center, and the aperture is therefore zero. When the blades 72a and 74 are moved away from each other, a given aperture is calculated by measuring the displacements of these blades from the central position.

Two pairs of supports 138 and 140 oppose each other along the direction of arrow 4 and extend upward from the base 98. Screw rods 134 and 136, which have the same construction as the screw rods 104 and 106 and which extend along the direction of arrow 4, are rotatably supported by the support pairs. As shown in FIG. 6, an engaging portion 142 is slidably fitted around the round portion of the screw rod 136, and the screw portion thereof is screwed into an engaging portion 144. An engaging portion is slidably fitted around the round portion of the screw rod 134, and the screw portion thereof is screwed into an engaging portion. The blade 76 is fixed on the lower surfaces of the engaging portion 142 and the engaging portion screwed around the screw portion of the screw rod 134. The blade 76 can reciprocate along the direction of arrow 4 upon rotation of the screw rod 134. On the other hand, the blade 78 is fixed on the lower surfaces of the engaging portion 144 and the engaging portion fitted around the round portion of the screw rod 134. Therefore, the blade 78 can reciprocate along the direction of arrow 4 upon rotation of the screw rod 136. The screw rod 136 is coupled to a stepping motor 146 through a coupling 148. Similarly, the screw rod 134 is coupled to a stepping motor (not shown). Position sensors 150 (see FIG. 5) which are provided to the blades 76, 78, respectively, generate signals when the blades 76 and 78 are located at a central position (a position immediately below the central position between the X-ray focal points L and R).

A pair of screw rods 152 and 154 (having the same construction as the screw rods 104 and 106) are rotatably supported between the upper supports 92 in the aperture device 70 and are parallel to each other along the direction of arrow 2. An engaging portion 156 is slidably fitted around the round rod portion of the screw rod 152, and the screw portion thereof is screwed into an engaging portion 158. The round portion and the screw portion of the screw rod 152 are the opposite of the screw rod 154. Engaging portions are engaged with the round and screw portions of the screw rod 154 in the same manner as in the screw rod 152. The blade 80 is fixed on the upper surfaces of the engaging portion 156 and the engaging portion screwed around the screw portion of the screw rod 154. The blade 82 is fixed on the upper surfaces of the engaging portion 158 and the engaging portion fitted around the round portion of the screw rod 154. The blade 82 is positioned above the blade 80 so as to overlap it. The screw rod 152 is coupled to a stepping motor 160 through a coupling 162, and the screw rod 154 is also coupled to a stepping motor (not shown) in the same manner. The screw rods 152 and 154 are rotated by the stepping motors 160 and the like, and the rotational motions of the screw rods 152 and 154 are converted to a reciprocal motion of the blades 80 and 82 along the direction of arrow 2 through the engaging portions 158 and the screw portions and the like. Position sensors 164 (see FIG. 6) for the blades 80 and 82 are mounted on the base 94, respectively. The position sensors 164 generate reference signals when the blades 80 and 82 are located at the center.

With reference to FIG. 5, two pairs of supports 170 and 172 are fixed on the lower surface of the base 94 and oppose each other along the direction of arrow 4. A screw rod 168 and a round rod 166 are rotatably supported by the respective support pairs and are parallel to each other along the direction of arrow 4. The screw rod 168 has a threaded portion on its entire surface. The screw rod 168 is screwed into an engaging portion 174. An engaging portion is slidably fitted around the round rod 166. The blade 84 is fixed on the engaging portion 174. The blade 84 has two circular holes 176 and 178. The centers of the circular holes 176 and 178 are spaced apart by a distance corresponding to that between the axes of the X-ray beams 64 and 66. The screw rod 168 is coupled to a stepping motor 180 through a coupling 182. The screw rod 168 is rotated by the stepping motor 180, so that the engaging portion 174 is moved along the direction of arrow 4. A sensor 184 is mounted on the lower surface of the base 94 to detect the blade 84. The sensor 184 generates a signal when the centers of the circular holes 176 and 178 coincide with the axes of X-ray beams 36 and 38, respectively.

A pair of supports 186 and 188 are fixed on the lower surface of the base 94 to be separated from each other in the direction of arrow 2. A horizontal base 190 is fixed on the supports 186 and 188. Supports 192 are fixed on the lower surface of the base 190. A disk-like base 200 is provided between the supports 192 and supported vertically through support members 194 such as bearings and supported horizontally through support members (not shown). A gear 202 is fixed on the lower surface of the base 200. A motor 204 is arranged on the base 190. A gear 206 is mounted on the rotating shaft of the motor 204 so as to mesh with the gear 202. Thus, the base 200 and the gear 202 are rotated by the motor 204.

Figure 8:
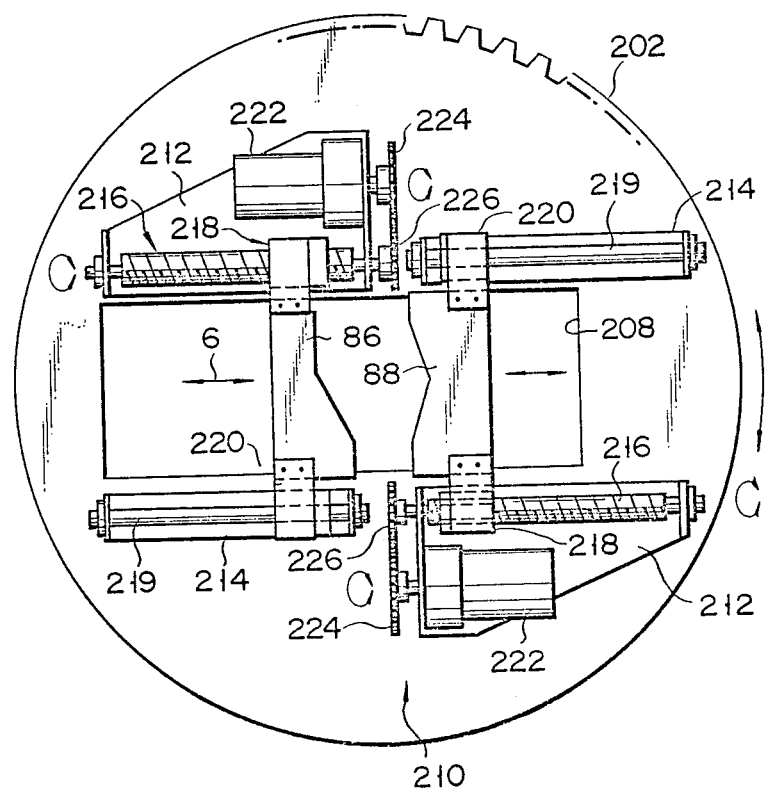
FIG. 8 is a schematic view showing a compensation filter mechanism.

An opening/closing mechanism 210 of the compensation filters 86 and 88 is arranged on the lower surface of the gear 202. The compensation filter opening/closing mechanism 210 is illustrated in FIG. 8, when the base 200 is viewed from the blades 72 and 74. A rectangular notch or window 208 extending along the direction indicated by arrow 6 is formed in the gear 202. Supports 212 and 214 are arranged along each of the long sides of the notch 208. The supports 212 and 214 along one long side oppose the supports 214 and 212 along the other long side through the notch 208, respectively. A screw rod 216 (having its entire peripheral surface threaded in the same manner as the screw rod 168) is rotatably supported by the support 212 and is parallel to the direction indicated by arrow 6. The screw rod 216 is screwed into an engaging portion 218. A direct current (DC) motor 222 is arranged on the support 212. A gear 224 is mounted on the rotating shaft of the DC motor 222. A gear 226 meshing with the gear 224 is mounted on the screw rod 216. When the motor 222 is rotated, the screw rod 216 is rotated through the gears 224 and 226. A round rod 219 is fixed on the support 214 and extends along the direction indicated by arrow 6. An engaging portion 220 is slidably fitted around the round rod 219. Filters 86 and 88 cross over a pair of engaging portions 218 and 220. The edges of the filters 86 and 88 opposed to each other are curved in a heart-like shape.

Figure 9:
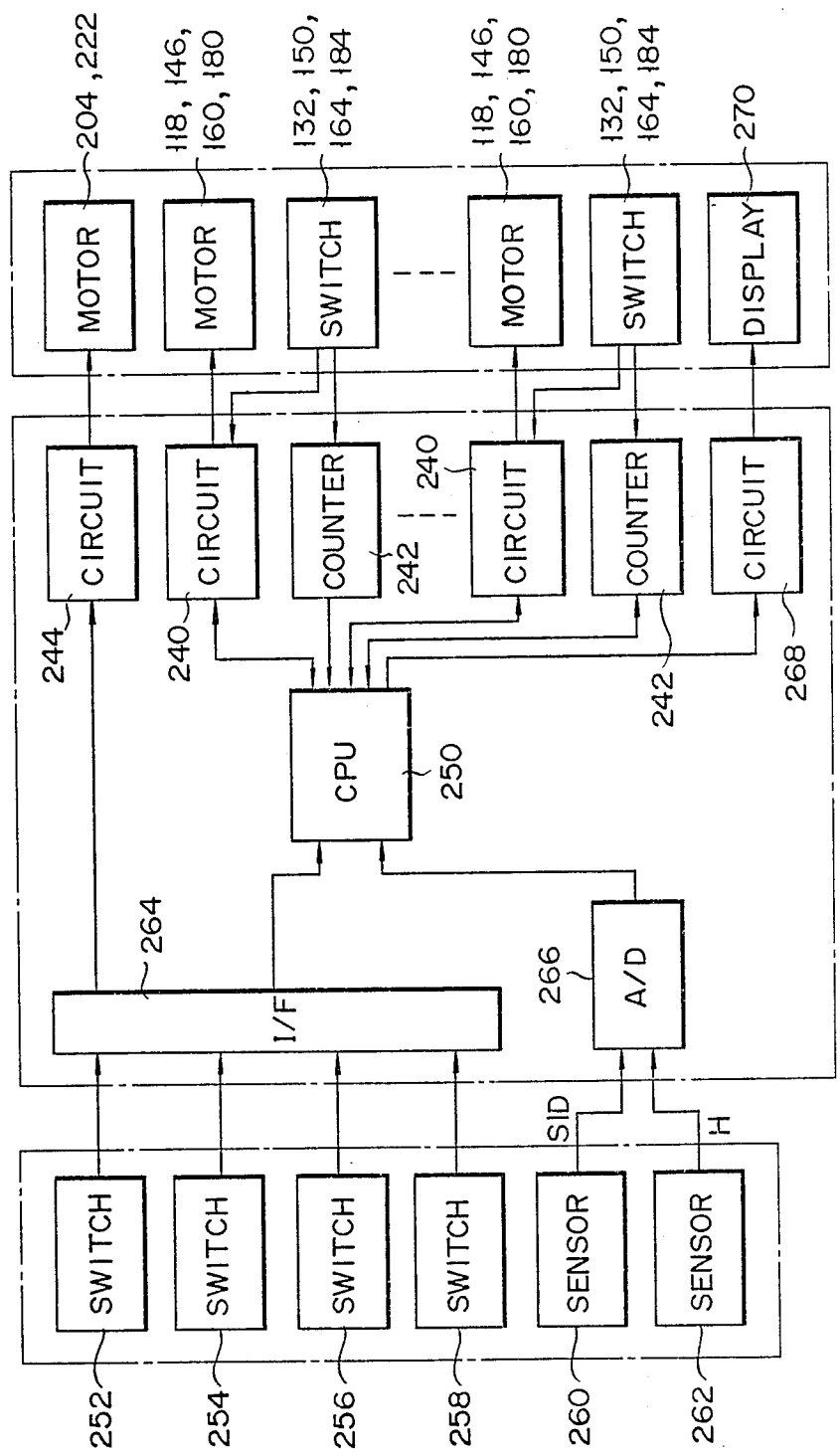
FIG. 9 is a block diagram of a control system.

The blades 72a, 72b, 74, 76, 78, 80, 82 and 84 and the filters 86 and 88 are made of a lead plate or a lead-containing acrylic resin plate which shields X-rays. The stepping motors 118, 146, 160 and 180 are driven by corresponding stepping motor drive circuits 240, as shown in FIG. 9. For every 100 pulses the drive circuit 240 generates, the stepping motor 118 is rotated by one revolution, for example. In other words, the stepping motor 118 is rotated by 3.6 degrees per one pulse. Upon one revolution of the stepping motor 118, and hence the screw rod 104, the engaging portion 112 is moved by a distance of 3 mm. The other drive circuits 240 for the stepping motors 146, 160 and 180 function in the same manner as the drive circuit for the stepping motor 118. Output pulses from the drive circuit 240 are also supplied to a corresponding counter 242. The counter 242 counts the pulses from the corresponding drive circuit 240. A count from the counter 242 is supplied to a CPU (central processing unit) 250. Outputs from the sensors 132, 150, 164 and 184 are supplied to the drive circuit 240 and then to the CPU 250. Motors 204 and 222 for the compensation filters are driven by a drive circuit 244.

An interface 264 is connected to a switch 252 for moving the blades to manually determine their positions, a switch 254 for switching between stereoscopic and monoscopic modes, a switch 256 for setting an image size and a switch 258 for switching between the I.I and the film changer. A sensor 260 for detecting the distance SID between the X-ray focal points L and R and the imaging surface, and a sensor 262 for detecting a distance H between the X-ray focal points L and R and the patient are connected to the CPU 250 through an A/D (analog-to-digital) converter 266. The sensors 260 and 262 may comprise potentiometers, respectively. An indicator or display 270 is connected to the CPU 250 through a drive circuit 268. The display unit 270 displays lengths and widths of the X-ray radiation area on the patient and the X-ray radiation area at the imaging surface.

The operation of the aperture device of the X-ray diagnosis apparatus will be described hereafter. Assume that the X-ray radiography mode is selected by the switch 258 and that the stereoscopic photography mode is selected by the switch 254. The blade 84 is located in the contracted position and the compensation filters 86 and 88 are fully opened. A length W2 of the X-ray radiation area at a desired imaging surface along the direction of arrow 2 and a length W4 thereof along the direction of arrow 4 are entered from the image size selection switch 256 to the CPU 250. Data SID and H are supplied from the sensors 260 and 262 to the CPU 250. The CPU 250 calculates the aperture size in accordance with these data.

Figure 10:
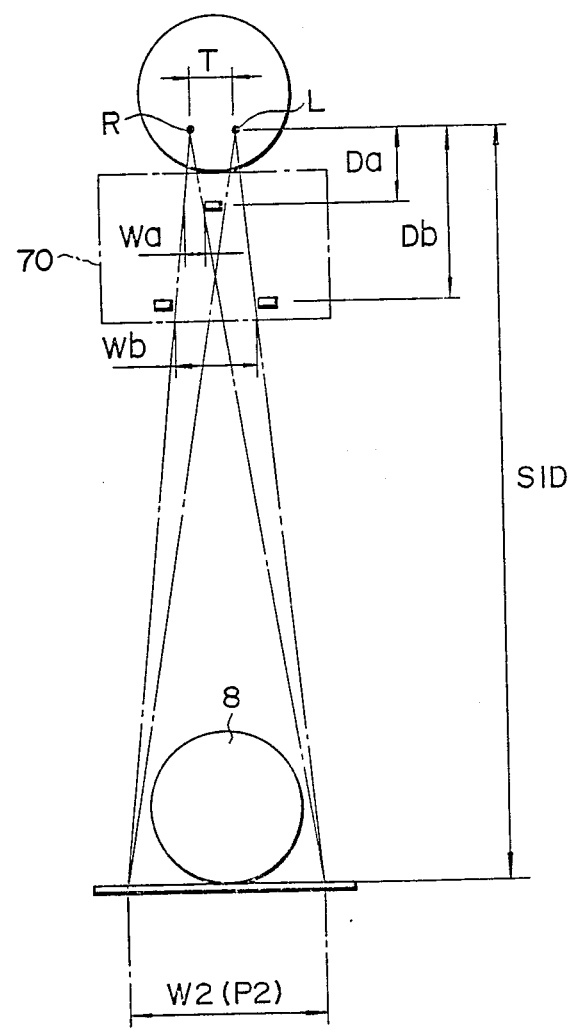
FIGS. 10 and 11 are views for explaining a calculation of an aperture size.

As shown in FIG. 10, assume that a distance between the X-ray focal points L and R is given as T, that a distance between the X-ray focal points L and R and the blades 80 and 82 is given as Da, and that a distance between the X-ray focal points L and R and the blades 72 and 74 is given as Db. Aperture sizes Wa and Wb at the blades 80 and 82 and the blades 72 and 74 are given by equations (1) and (2) as follows:

$$Wa = W2 \times Da/SID \quad (1),$$

$$Wb = (W2 - T) \times Db/SID + T \quad (2).$$

Figure 11:
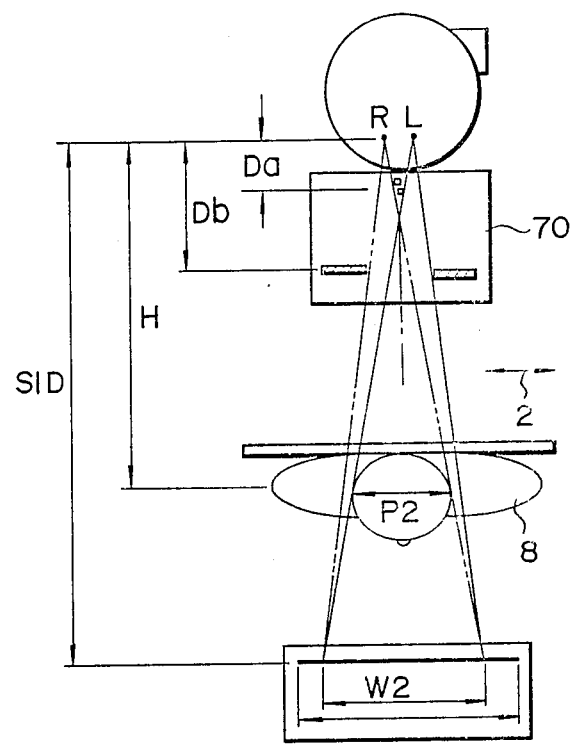
Figure 12:
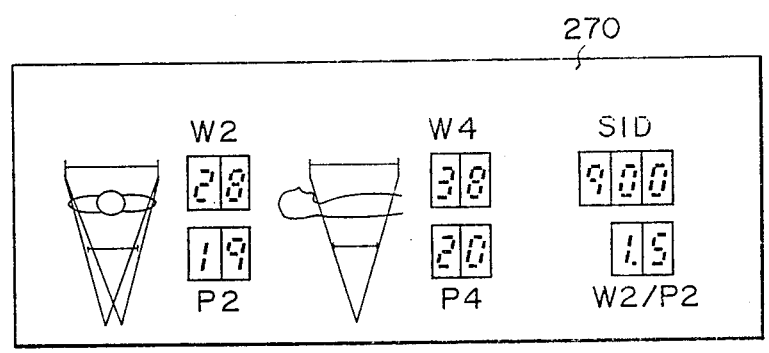
FIG. 12 is a front view of an indicator or display unit.

An aperture size Wc at the blades 76 and 78 is given as follows:

$$Wc = W4 \times Dc/SID \quad (3),$$

where Dc is the distance between the X-ray focal points L and R and the blades 76 and 78. Values Da, Db, Dc and T are constants. When data SID, W2 and W4 are given, the CPU 250 calculates the sizes Wa, Wb and Wc in accordance with equations (1), (2) and (3). When the enlarged stereoscopic radiography shown in FIG. 11 is performed unlike the contact stereoscopic radiography shown in FIG. 10, lengths P2 and P4 of the X-ray radiation area of the patient 8 along the directions of arrows 2 and 4 are given by the mathematical expression $P_2 = W_2 \times H/SID + T \times [(H/SID) - 1]$ and $W4 \times (H/SID)$, respectively. The resultant values are displayed on the display 270 through the drive circuit 268. FIG. 12 shows an example of the display 270. Lengths W2 and P2 of the X-ray radiation areas at the imaging surface and the patient along the direction of arrow 2, and lengths W4 and P4 of the X-ray radiation areas at the imaging surface and the patient along the direction of arrow 4 are displayed on the display 270. In addition, the distance SID and a magnification ratio W2/P2 of the image are also displayed.

Thus, the lengths W2, P2, W4 and P4 of the X-ray radiation areas are displayed. Therefore, in the under-tube system shown in FIG. 11, the X-ray radiation area which cannot be performed pre-adjustment by the conventional aperture device can be checked before X-ray radiation. Thus, according to the embodiment, the under-tube system can be used more effectively.

The aperture sizes Wa, Wb and Wc of the blades 80 and the blade 82, the blades 72 and 74, and the blades 76 and 78 are supplied from the CPU 250 to the drive circuits 240 of the stepping motors 160, 118 and 146. The drive circuits 240 drive the stepping motors 118, 146 and 160 to move the blades 72, 74, 76, 78, 80 and 82 toward the center. When the blades 72, 74, 76, 78, 80 and 82 are located in the central positions, respectively, the switches 132, 150 and 164 supply the detection signals to the drive circuits 240 to stop the stepping motors 118, 146 and 160. At the same time, the detection signals are supplied to the counters 242 which are then cleared. The drive circuits 240 generate the necessary pulses to drive the stepping motors 118 or the like so as to move the blades 72, 74, 76, 78, 80 and 82 to the predetermined positions in accordance with the aperture sizes Wa, Wb and Wc. The blades 72 and the like are thus moved. The blades 72, 74, 76, 78, 80 and 82 are located in the positions shown in FIG. 13 so as to define the X-ray beams 64 and 66 from the X-ray focal points L and R, thereby obtaining a desired rectangular shape. In this manner, the apertures are automatically set.

However, the X-ray radiation area must be further decreased in accordance with the type of diagnosis. In this case, the switch 252 is operated to start the drive circuits, thereby rotating the stepping motor 118 and the like hence moving the blades 72 and the like to form a smaller aperture. The counts of the counters 242 are also supplied to the CPU 250. The CPU 250 calculates the aperture sizes Wa, Wb and Wc in accordance with the counts. The CPU 250 also calculates the lengths W2 and W4 of the X-ray radiation areas at the imaging surface along the directions of arrows 2 and 4, and the lengths P2 and P4 of the X-ray radiation areas of the patient along the directions of arrows 2 and 4 in accordance with equations (1), (2) and (3). These updated data W2, W4, P2 and P4 are supplied from the CPU 250 to the drive circuit 268 and are displayed on the display unit 270. In this manner, after the aperture device 70 is adjusted, the X-ray beams 64 and 66 are emitted alternately for a predetermined period of time, thereby alternately exposing the left and right X-ray transmitted images.

According to this aperture device, the blades 72, 74, 76, 78, 80 and 82 can be located at variable positions with high precision, and the X-ray radiation area can be adjusted to be identical with a predetermined diagnosis area with high precision. Therefore, in stereoscopic radiography, the patient will not be irradiated by unnecessary X-rays. Even if the distance SID changes, the aperture sizes Wa, Wb and Wc can be calculated in accordance with equations (1), (2) and (3), so that the respective blades can be automatically adjusted. In addition, the updated aperture sizes are displayed on the display. The operator can manually adjust the positions of the respective blades in accordance with the results displayed on the display. Even in the under-tube system, the X-ray radiation area can be checked before X-ray radiation.

Figure 14:
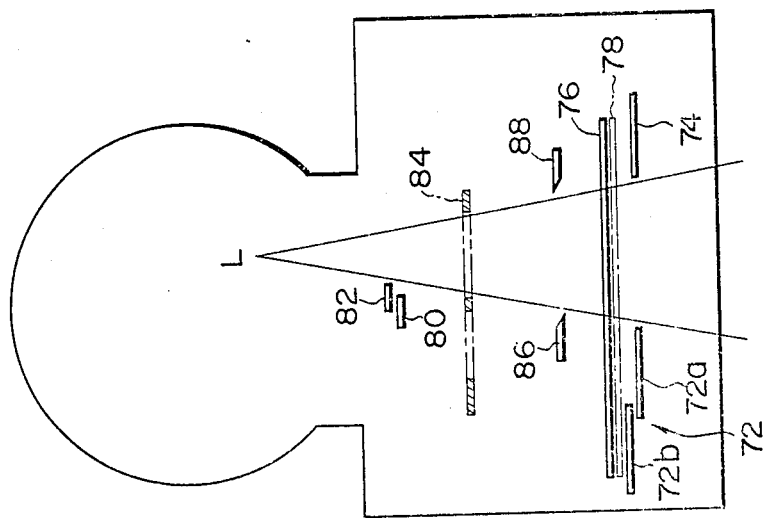
FIGS. 13 and 14 are representations for explaining the operation of the aperture device.
Figure 13:
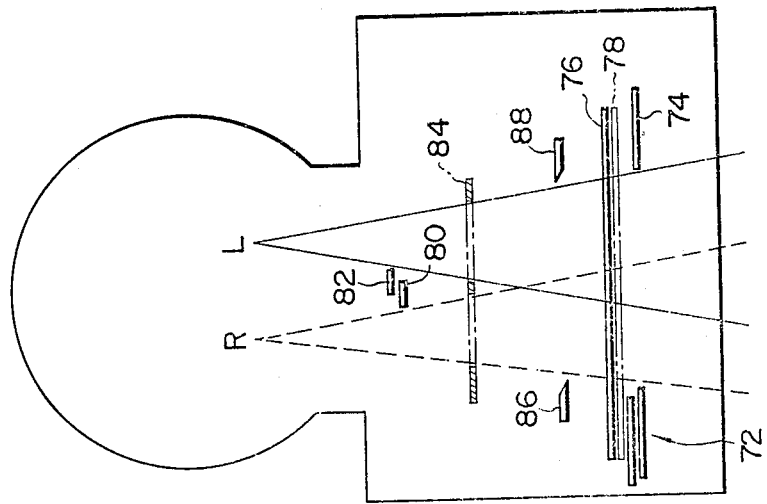

When monoscopic radiography is selected by the switch 254, the X-ray is emitted from the left X-ray focal point L, as shown in FIG. 14. In the same manner as in stereoscopic radiography, the drive circuits 240 and the counter 242 cause the stepping motors 118 and the like to rotate in response to the signals from the CPU 250 so as to move the respective blades to the predetermined positions. In this case, the blades 72 comprise two blades 72a and 72b, as shown in FIG. 7. When the screw rod 106 is rotated by the rotation of the stepping motor, the engaging portion 114 is moved toward the blade 74. The blade 72b having the lock portion 130 engaged in the notch 122 of the blade 72a is moved together with the blade 72a toward the blade 74. As a result, the blade 72a abuts against the blade 72b, and the blades 72a and 72b shield the X-ray at a large area having a length corresponding to a sum of lengths of the blades 72a and 72b along the direction of arrow 2. However, as shown in FIG. 13, when stereoscopic radiography is performed, the blades 72a and 72b substantially overlap each other. Since the blades 72 comprise two blades, the X-rays can be focused in the stereoscopic radiography and monoscopic radiography, thus enabling a compact construction.

When cardiac angiography is performed, X-rays are readily transmitted by the lungs. In a transmitted X-ray image, the lung portion is abnormally bright. In order to prevent halation of an image representing the lung portion, the compensation filters 86 and 88 are used. The switch 254 is set in the monoscopic mode, and the switch 258 is set in the I.I mode. The switch 252 is operated to start a compensation filter drive circuit 244 to activate the motors 204 and 222. Upon activation of the motor 222, the filters 86 and 88 are moved in the direction of arrow 6 (see FIG. 8) and are stopped such that the opposing edges of the filters 86 and 88 correspond to the opposing edges of the heart. In this case, the motor 204 is activated to rotate the base 200. The X-ray fluoroscopic area surrounded by the filters 86 and 88 can easily match with the shape of the heart. The switch 258 is set in the X-ray radiography mode as needed and cardiac angiography can be performed while the halation is prevented.

When stereoscopic X-ray fluoroscopy is performed by the I.I, the switch 258 is set at the I.I position. The motors 118, 146 and 160 are activated to move the blades 72, 74, 76, 78, 80 and 82 so as to obtain a condition that the edges of the X-ray beams 64 and 66 are shut off. However, the CPU 250 causes the drive circuit 240 to activate the stepping motor 180. The blade 84 is moved from the withdrawn position toward the center position. When the blade 84 is located at a position immediately under the center between the X-ray focal points L and R, the sensor 184 generates a signal which is then supplied to the CPU 250 through the drive circuit 240. When the CPU 250 receives the detection signal from the sensor 184, the CPU 250 causes the drive circuit 240 and hence the stepping motor 180 to stop. The blade 84 is stopped at the position where the centers of the holes are located on the lines which connect the X-ray focal points L and R and the central position of the image receiving surface. The X-ray beams 64 and 66 from the X-ray focal points L and R are defined by the blade 84 so as to form a circular radiation area.

When a monoscopic X-ray fluoroscopy is performed, the blade 72 is operated to shut off the edge of the X-ray beam 66 in order to eliminate an influence of an X-ray scattered by the blade 82 and to further sharpen the edge of the X-ray beam 66.

What is claimed is:

1. An aperture device of a radiation diagnostic apparatus which defines first and second radiation beams omitted from two radiation focal points spaced apart from each other along a first direction, the first and second radiation beams being defined by the aperture device to selectively form a radiation area in stereoscopy or monoscopy, the two radiation focal points also being spaced from an imaging surface in another direction and the apparatus including means for selectively changing the distance between the focal points and the imaging surface, the aperture device comprising:

first and second blades, made of a radiation shielding material and movable along the first direction, for respectively defining, during selected stereoscopic operation, inner and outer edges of the first radiation beam along the first direction;

first and second drive means for respectively driving said first and second blades;

third and fourth blades, made of a radiation sheilding material and movable along the first direction, for respectively defining, during selected stereoscopic operation, inner and outer edges of the second radiation beam along the first direction, said second and fourth blades overlapping each other in the first direction;

third and fourth drive means for respectively driving said third and fourth blades;

fifth and sixth blades, made of a radiation shileding material and movable along a second direction transverse to the first direction, for respectively defining two edges of each of the first and second radiation beams along the second direction;

fifth and sixth drive means for respectively driving said fifth and sixth blades, the first radiation beam being defined by said first, second fifth, and sixth blades in a rectangular shape, and the second radiation beam being defined by said third, fourth, fifth and sixth blades in a rectangular shape;

adjusting means for automatically adjusting the position of said first to sixth blades to define the radiation area to be identical with a predetermined diagnostic area in accordance with the change of the distance between the X-ray focal points and the imaging surface; and means associated with said first blade for obscuring said first radiation beam during selective monoscopy operation, said obscuring means including a progressive, double slide-type first blade for defining the edge of the second beam opposed to the edge defined by said third blade during operation of the second beam only.

2. The aperture device of claim 1 wherein said double slide-type first blade includes a first blade member and
   (i) an auxiliary blade, (ii) an auxiliary blade supporting means for supporting said auxiliary blade for movement in the first direction, (iii) an ear formed in said first blade member, said ear having a notch extending along the first direction, and (iv) a lock portion formed in said auxiliary blade engageable with said notch in said ear, said auxiliary blade being movable when said lock portion is engaged with said notch when said first blade member is moved in the first direction.

3. A compact aperture device of a radiation diagnostic apparatus which defines first and seocnd radiation beams emitted form two radiation focal points spaced apart from each other along a first direction, comprising:

first and second blades, made of a radiation shielding material and movable along the first direction, for respectively defining outer and inner edge of the first radiation beam along the first direction;

first and second drive means for respectively driving said first and second blades;

third and fourth blades, made of a radiation shielding material and movable along the first direction, for respectively defining outer and inner edges of the second radiation beam along the first direction, said second and fourth blades overlapping each other in the first direction;

third fourth drive means for respectively driving said third and fourth blades;

fifth and sixth blades, made of a radiation shield material and movable along a second direction transverse to the first direction, for respectively defining two edges of each of the first and second radiation beams along the second direction; and fifth and sixth drive means for respectively driving said fifth and sixth blades, the first radiation beam being defined by said first, second, fifth and sixth blades in a rectangular shape, and the second radiation beam being defined by said third, fourth, fifth and sixth blades in a rectangular shape, wherein each of said first to sixth drive means comprises:

a pair of screw rods each having a round portion and a screw portion, said pair of screw rods being parallel to each other in such a manner that said round and said screw portions of one of said pair of screw rods oppose those of the other thereof;

a first engaging portion into which said screw portion is screwed;

a second engaging portion slidably fitted around said round portion so as to support a corresponding one of said first to sixth blades together with said first engaging portion; and a motor for rotating the screw rod engaged with the first engaging portion, said corresponding one of said first to sixth blades being moved parallel to said pair of screw rods upon rotation of said motor and the corresponding one of said pair of screw rods, wherein said motor comprises a stepping motor;

the aperture device further comprising: a drive circuit for generating a pulse for activating said stepping motor; a counter for counting an output pulse from said drive circuit; a sensor for supplying a detection signal to said counter when the corresponding one of said first to sixth blades is moved to a predetermined position, and for clearing a count of said counter; and a central processing unit for calculating a blade displacement distance from the predetermined position of said corresponding blade in accordance with the count of said counter.

4. A compact aperture device of a radiation diagnostic apparatus which defines first and second radiation beams emitted from two radiation focal points spaced apart from each other along a first direction, comprising:

first and second blades, made of radiation shielding material and movable along the first direction, for respectively defining outer and inner edges of the first radiation beam along the first direction;

first and second drive means for respectively driving said first and second blades;

third and fourth blades, made of a radiation shielding material and movable along the first direction, for respectively defining outer and inner edges of the second radiation beam along the first direction, said second and fourth blades overlapping each other in the first direction;

third and fourth drive means for respectively driving said third and fourth blades;

fifth and sixth blades, made of a radiation shielding material and movable along a second direction transverse to the first direction, for respectively defining two edges of each of the first and second radiation beams along the second direction; and fifth and sixth drive means for respectively driving said fifth and sixth blades, the first radiation beam being defined by said first, second, fifth and sixth blades in a rectangular shape, and the second radiation beam being defined by said third, fourth, fifth and sixth blades in a rectangular shape, the aperture device further comprising: a seventh blade made of a radiation shielding material and having two radiation transmission holes formed at positions spaced apart from each other along the first direction; and seventh drive means for driving said seventh blade between a withdrawn position and a beam shielding position where said seventh blade is located in an optical path of the radiation beam, the radiation beam being defined to form a circular radiation spot when said seventh blade is located in the beam shielding position.

5. The aperture device according to claim 4, wherein said seventh drive means comprises;

a pair of screw rods each of which has a round portion and a screw portion, said pair of screw rods being parallel to each other in such a manner that said round and screw protions of each of said pair of screw rods oppose those of the other thereof;

a third engaging portion into which said screw portion is screwed;

a fourth engaging portion slidably fitted around said round portion for supporting the corresponding blade together with said third engaging portion; and a motor for rotating the screw rod engaged with the third engaging portion, said third and fourth engaging portions and said corresponding blade being movable parallel to said pair of screw rods upon rotation of said motor and the corresponding one of said screw rods.

6. The aperture device according to claim 5 wherein said motor comprises a stepping motor.

7. A compact aperture device of a radiation diagnostic apparatus which defines first and second radiation beams emitted from two radiation focal points spaced apart from each other along a first direction, comprising:

first and second blades, made of a radiation shielding material and movable along the first direction, for respectively defining outer and inner edges of the first radiation beam along the first direction;

first and second drive means for respectively driving said first and second blades;

third and fourth blades, made of radiation shielding material and movable along the first direction, for respectively defining outer and inner edges of the second radiation beam along the first direction, said second and fourth blades overlapping each other in the first direction;

third and fourth drive means for respectively driving said third and fourth blades;

fifth and sixth blades, made of a radiation shielding material and movable along a second direction transverse to the first direction, for respectively defining two edges of each of the first and second radiation beams along the second direction; and fifth and sixth drive means for respectively driving said fifth and sixth blades, the first radiation beam being defined by said first, second, fifth and sixth blades in a rectangular shape, and the second radiation beam being defined by said third, fourth, fifth and sixth blades in a rectangular shape, the aperture device further comprising a compensation filter mechanism, said compensation filter mechanism having:

a rotatable base having a window through which the radiation passes;

base drive means for rotating said base;

a pair of filters arranged in said window of said base and made of a radiation shieldign material, said filters having opposing edges which constitute the shape of a heart; and filter drive means for moving said filters relative to said base, said filters being movable toward or away from each other, said filters when moved toward each other preventing a halation at a lung portion when cardiac angiography is performed, wherein said filter drive means comprises:

a round rod;

a screw rod which is parallel to the round rod;

a motor for rotating the screw rod;

a fifth engaging portion slidably fitted around the round rod; and a sixth engaging portion into which said screw rod is screwed so as to support a corresponding one of said filters together with said fifth engaging portion, wherein the fifth and sixth engaging portions and the corresponding filter are moved parallel to the round rod and screw rod upon rotation of said motor.

8. A compact aperture device of a radiation diagnostic apparatus which defines first and second radiation beams emitted from two radiation focal points spaced apart from each other along a first direction, comprising:

first and second blades, made of a radiation shielding material and movable along the first direction, for respectively defining outer and inner edges of the first radiation beam along the first direction;

first and second drive means for respectively driving said first and second blades;

third and fourth blades, made of a radiation shielding material and movable along the first direction, for respectively defining outer and inner edges of the second radiation beam along the first direction, said second and fourth blades overlapping each other in the first direction;

third and fourth drive means for respectively driving said third and fourth blades;

fifth and sixth blades, made of a radiation shielding material and movable along a second direction transverse to the first direction, for respectively defining two edges of each of the first and second radiation beams along the second direction; and fifth and sixth drive means for respectively driving said fifth and sixth blades, the first radiation beam being defined by said first, second, fifth and sixth blades in a rectangular shape, and the second radiation beam being defined by said third, fourth, fifth and sixth blades in a rectangular shape, said aperture device having means to define first and second radiation beams which are irradiated on an image receiving surface after being transmitted through a patient, and which aperture device further comprises detecting means for detecting a distance SID from the focal points of the radiation beams to the image receiving surface, a distance H from said focal points ofs the radiation beams to the patient and aperture widths W of the first through the sixth blades, a calculating circuit for the calculating radiation areas at the image receiving surface and the patient on the basis of the distances SID and H and the aperture widths W, and display means or dispalying the radiation areas at the image receiving surface and the patient.

9. An aperture device of a radiation diagnostic apparatus which defines edges of radiation beam along a first direction and a second direction transverse thereto, which beam is emitted from a focal point and irradiated on an image receiving surface after being transmitted through a patient, comprising:

first and second blades, made of a radiation shielding material and movable along the first direction, for respectively defining two edges of the radiation beam along the first direction;

first and second drive means for respectively driving said first and second blades;

third and fourth blades, made of a radiation shielding material and movable along the second direction, for respectively defining two edges of the radiation beam along the second direction;

third and fourth drive means for respectively driving said third and fourth blades, the radiation beam being defined by said first, second, third and fourth blades in a rectangular shape;

detecting means for detecting a distance SID from the focal point of the radiation beam to the image receiving surface, a distance H from said focal point of the rasdiation beam to the patient, and aperture widths W of the first through the fourth blades;

a calculating circuit for calculating radiation areas at the image receiving surface and the patient as a function of the distances SID and H and the aperture widths w; and display means for displaying the radiation areas at the image receiving surface and the patient.

* * * * *